United States Patent
Fujisaki et al.

[11] Patent Number: 5,935,520
[45] Date of Patent: Aug. 10, 1999

[54] DRY ANALYTICAL ELEMENT

[75] Inventors: Yasushi Fujisaki; Sigeru Tezuka; Hikaru Tsuruta; Osamu Seshimoto, all of Saitama, Japan

[73] Assignee: Fuji Photo Film Co., Ltd., Kanagawa, Japan

[21] Appl. No.: 08/628,975

[22] Filed: Apr. 8, 1996

Related U.S. Application Data

[63] Continuation of application No. 08/230,386, Apr. 20, 1994, abandoned.

[30] Foreign Application Priority Data

Apr. 20, 1993 [JP] Japan .................................. 5-093369

[51] Int. Cl.$^6$ .................................................. G01N 33/48
[52] U.S. Cl. ............................. 422/58; 422/66; 436/46; 436/169
[58] Field of Search ................. 422/56–58, 66; 435/805; 436/46, 169

[56] References Cited

U.S. PATENT DOCUMENTS

| | | | |
|---|---|---|---|
| 2,129,754 | 9/1938 | Yagoda | 23/253 |
| 2,785,057 | 3/1957 | Schwab et al. | 422/58 |
| 3,992,158 | 11/1976 | Przybylowicz et al. | 422/65 |
| 4,477,575 | 10/1984 | Vogel et al. | 436/170 |
| 4,647,430 | 3/1987 | Zweig | 422/58 |
| 4,776,904 | 10/1988 | Charlton et al. | 422/56 |
| 5,209,904 | 5/1993 | Forney et al. | 436/46 |

FOREIGN PATENT DOCUMENTS

| | | |
|---|---|---|
| 0185982 | 7/1986 | European Pat. Off. . |
| 0209032 | 1/1987 | European Pat. Off. . |
| 0443231 | 8/1991 | European Pat. Off. . |

*Primary Examiner*—Lyle A. Alexander
*Attorney, Agent, or Firm*—McAulay Nissen Goldberg Kiel & Hand, LLP

[57] ABSTRACT

A dry analytical substantially flat film chip for use as an analytical element composed of a support, at least one reagent layer and a spreading layer laminated in this order. The chip is suitable for use as is as an analytical element for liquid samples. The chip further has means for restraining a liquid sample applied to its surface from spreading beyond a predetermined area of the surface. The restraining means may be a fused nonporous area of the spreading layer or may be a portion or area of the spreading layer which has been clogged with a hydrophobic or lipophilic material to render it nonporous. The inventive film chip, in addition, provides means for preventing fraying of the edges of the porous spreading layer as well as the prevention of the generation of fiber dust during cutting of the chip.

18 Claims, 6 Drawing Sheets

DRY ANALYTICAL ELEMENT

This is a continuation of application Ser. No. 08/230,386, filed Apr. 20, 1994 now abandoned.

BACKGROUND OF THE INVENTION

This invention relates to a dry analytical film chip which is a small piece of dry analytical film cut into a specific form, such as square, rectangle, circle or ellipsoid. The dry analytical film has a reagent layer wherein chemical reaction, biochemical reaction or immunological reaction occurs with a predetermined biochemical substance (hereinafter referred to as analyte) contained in a sample solution, such as blood or urine to produce an optical density change.

In general, to analyze qualitatively or quantitatively a specific component or an activity of a specific component in a sample solution is conducted in various industrial fields. Particularly, it is very important to analyze quantitatively the content or activity of a biochimical component or the content of a solid component of a body fluid, such as blood or urine, of an organism in the field of linical biochemical analysis.

Recently, various dry integral multilayer analytical films (also called multilayer analytical element) have been developed which can determine the content or activity of a specific analyte or the content of a specific solid component by merely spotting a small droplet of a sample solution (JSP 3,992,158, U.S. Pat. No. 4,292,272, Japanese Patent KOKAI No. 57-42951, etc.), and put to practical use. Filter paper-type test pieces and modifications thereof composed of single layer or multilayers were also proposed (U.S. Pat. No. 4,477,575), and are, in part, put to practical use. Since a sample solution can be analyzed simply and rapidly by using the dry analytical films compared with conventional wet analysis to use the dry analytical films is particularly useful for a medical organization or laboratory where a great number of sample solutions are analyzed.

As a method of analyzing an analyte of a sample solution quantitatively by using the dry analytical film, the sample solution was spotted onto the dry analytical film (when there is a spreading layer, onto the spreading layer, on the other hand, when there is no spreading layer, onto the reagent layer directly), and is kept at a definite temperature (incubated) for a predetermined period in an incubator (oven) to induce a coloring reaction (dye-forming reaction). Subsequently, light for measurement containing a wavelength, which has been previously selected by the combination of a specific analyte in a sample solution and a reagent contained in a dry analytical film, is irradiated to the dry analytical film, and the optical density is measured. The concentration or activity of the analyte in the sample solution is determined by applying the optical density to a calibration curve indicating the correlation between the optical density and the concentration or activity of the analyte which has been previously determined.

The above dry analytical film is composed of at least one layer of a reagent layer provided on a support formed of an organic polymer, preferably further a spreading layer provided on the upper side of the reagent layer. The dry analytical film is formed into a chip, and put in a slide frame made of organic polymer (called analytical slide) in order to treat by automatic operation. The slide frame also functions to keep the dry analytical film flat which tends to deform in dry conditions.

However, analyzers using the above analytical slides tend to be a big apparatus. That is, in a big medical organization, since a great quantity of analytical slides is expended in a short period, a big size cartridge is used. Moreover, it is necessary to provide the number of cartridges corresponding to the number of the analytes, and thereby, the space for setting cartridge becomes large.

Besides, the cost of the slide frame is great, and elevates the cost of the analytical slide, and the presence of the slide frame itself makes the size of cartridges and incubator greater.

Thereupon, the inventors developed an analyzer for dry analysis which can use dry analytical film chips as it is (without mounted in a slide frame) (EP 0 567 057 A).

Figure 13:
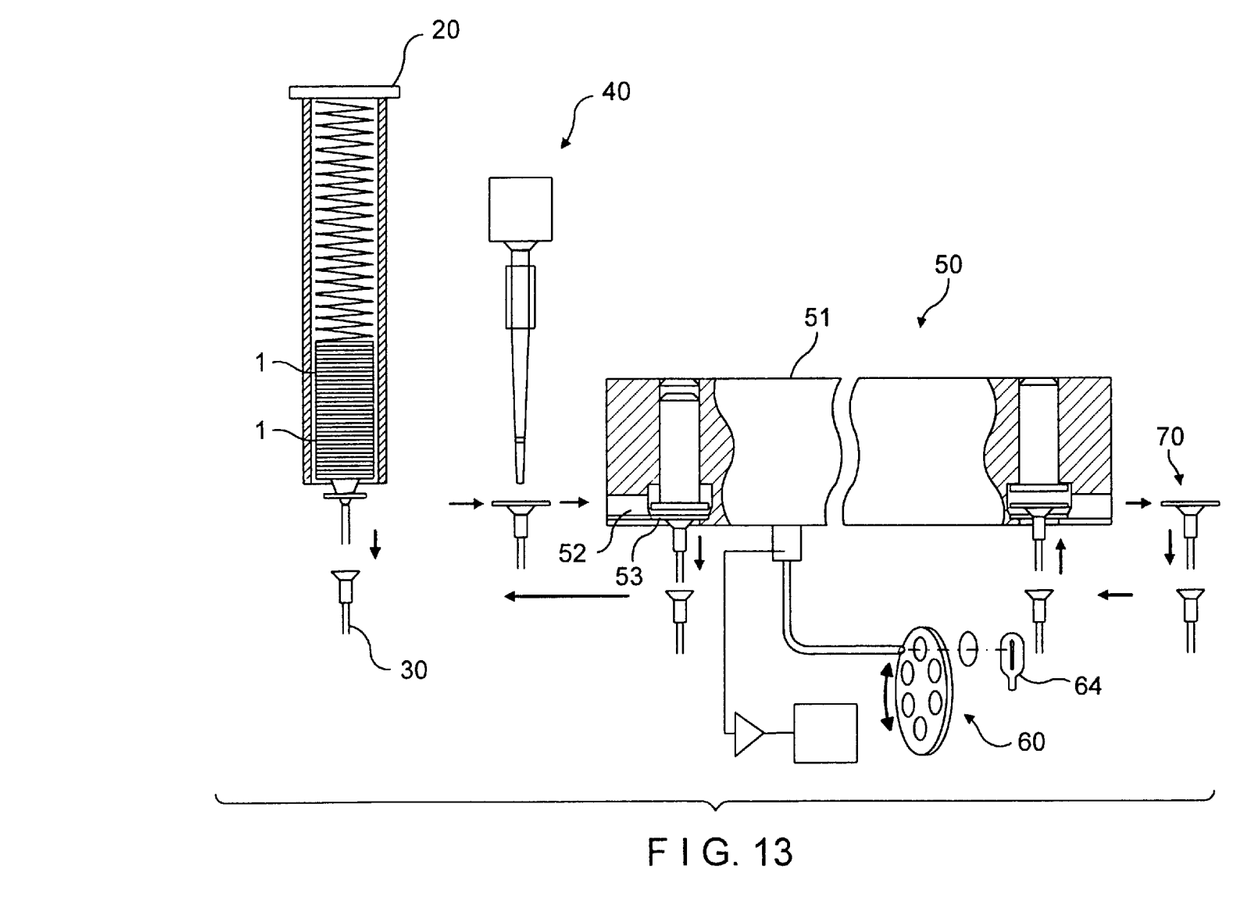
FIG. 13 is a schematic side view partially in section of an analyzer using the dry analytical film chips of the invention.

A representative embodiment of the analyzer for dry analysis is, as shown in FIG. 13, provided with a dry analytical film chip storing portion 20 for storing virgin dry analytical film chips 10, a dry analytical film chip conveying portion 30 for taking out the dry analytical film chips 10 from the storing portion 20 and delivering to the incubator described below, a spotting portion 40 for spotting a liquid sample onto the dry analytical film chip 10 during conveying in the conveying portion 30, an incubator 50 for keeping the dry analytical film chip 10 onto which the sample liquid has been spotted at a constant temperature for a predetermined time, a photometric portion 60 for measuring the reflection optical density of the dry analytical film chip 10 wherein a coloring reaction has occured in the incubator 50, and a discharge portion 70 of the dry analytical film chip for discharging the dry analytical film chip 10 which has been measured at the photometric portion 60 from the incubator 50.

In the incubator 50, an incubator body 51 in a disc form is rotatably supported. The incubator body 51 contains a heating means (not illustrated) which keep the inside at a constant temperature around 37° C. Many insertion holes 52 are formed on the circumferential side end of the body 51 at regular intervals for inserting the dry analytical film chip 10, and followed by placing parts 53 for placing the dry analytical film chip 10.

Figure 14:
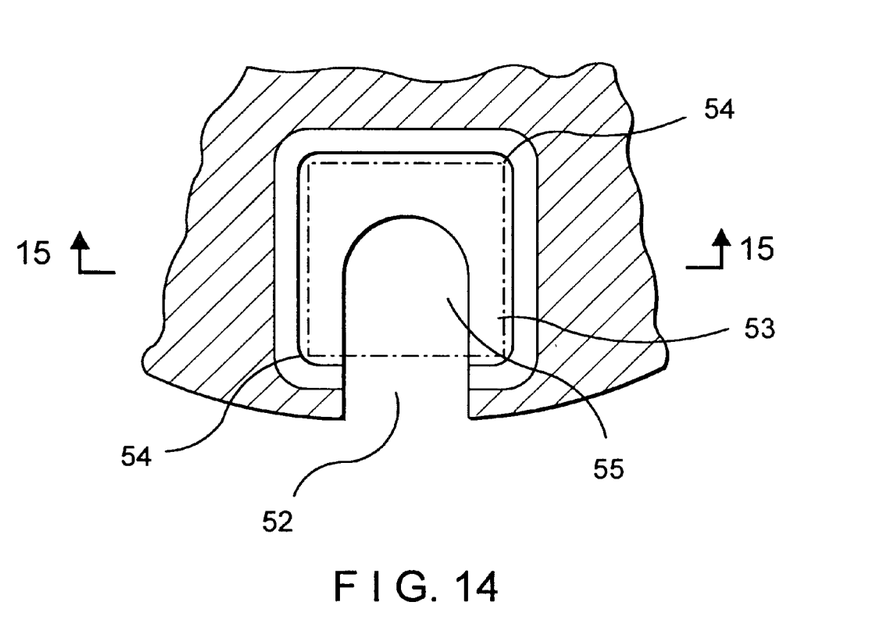
FIG. 14 is a lateral section of the placing part of the incubator of the analyzer.
Figure 15:
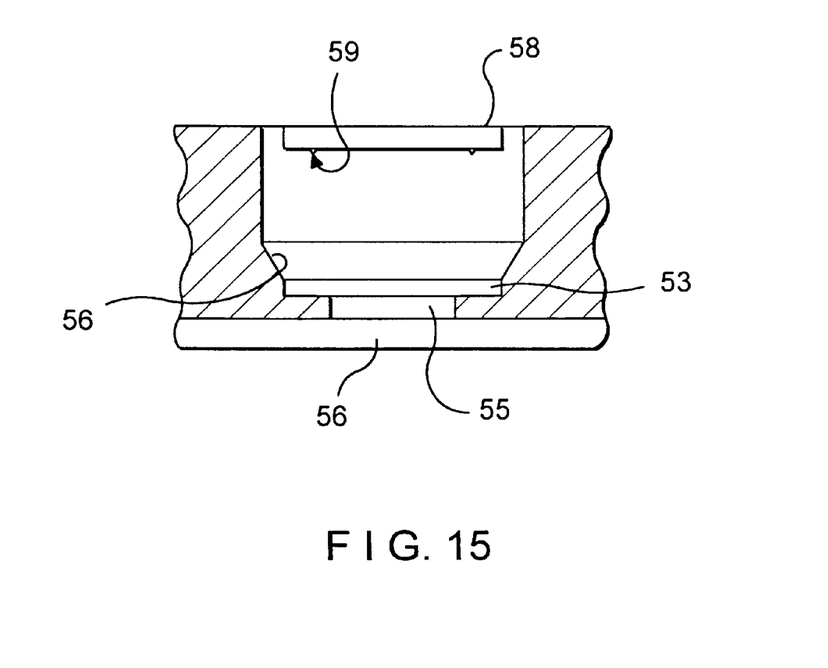
FIG. 15 is a section along line A—A of FIG. 14.

As shown in FIGS. 14 and 15, the placing part 53 has a rectangular planar form greater than the dry analytical film chip 10, and each corner 54 is projected toward the inside by rounding. Each corner of the dry analytical film chip 10 is caught by the rounded corner 54, and thereby, the sides edges of the dry analytical film chip 10 do not contact the side walls of the placing part 53. A photometric window 55 is formed at the center of the placing part 53, and a ring groove 56 into which a photometric head described later enters is formed at the underside of the photometric window 55. A taper 57 is formed above the periphery of the placing part 53 in order to guide the dry analytical film chip 10, and a cover 58 is provided movable in the vertical direction above the placing part 55 so as to prevent the evaporation of the liquid sample. Moreover, presser zigs 59 are formed at four corner portions on the underside of the cover 58 in order to rectify the deformation of the dry analytical film chip 10 by pressing.

However, it was found that, in the above analyzer using the conventional dry analytical film chips, when the dry analytical film chip has a spreading layer composed of a microporous material, liquid sample spreads to reach ends of the spreading layer and effuses from the edges. In the case of a liquid sample having a low viscosity, the liquid sample diffuses on the surface of a spreading layer or a reagent layer (particularly, in the case of a dry analytical film chip not having a spreading layer) a reagent layer to reach edges of the reagent layer, and effuses from the edges. As a result, there is a possibility that the analyzer is stained at the incubator, the photometric portion, the discharging portion, or the like, or another dry analytical film chip which has been spotted with a liquid sample but not measured photometrically yet is stained (or contaminated).

That is, since the dry analytical film chip is deformed by drying, it is pressed by the cover having the presser zigs at the placing part of the dry analytical film chip in the incubator. Accordingly, if the liquid sample spotted onto the dry analytical film chip spreads to reach the vicinity of four (4) corners, when the presser zigs press the dry anaytical film chip, the presser zigs are stained by adhering the liquid sample. The subsequent dry analytical film chip is pressed by the stained presser zigs, and results in stained by the previous liquid sample.

Moreover, if the liquid sample which has reached edges of the dry analytical film chip by spreading effuses from the edges, the edges are wet by the liquid sample. Since the placing part for the dry analytical film chip in the incubator is arranged so that the inner wall of the placing part contact edge of four corners of the dry analytical film chip in order to position the dry analytical film chip, the liquid sample spotted onto the dry analytical film chip adheres onto the wall of the placing part at the contact position, and occasionally stains the bottom of the placing part as well as the wall portion. The adhered liquid sample stains the next dry analytical film chip.

Since the dry analytical film chips are transferred to the photometric portion, the discharging portion and the like successively, the liquid sample effused from edges adheres to stain the photometric portion, the discharging portion and the like. Particularly, when the liquid sample is a biological body fluid represented by blood, the incubator is stained by the biological body fluid at the incubator, the presser zigs, the photometric portion, the discharging portion or the like. Since the body fluid has a possibility to contain pathogenic bacteria, fungi or viruses, the analyzing operator is in danger of falling into the infection with them. Accordingly, it is very undesirable is sanitary viewpoint.

The above staining troubles can be aboided by reducing the spotting amount of liquid samples, but measuring accuracy is degraded thereby.

Furthermore, the aforementioned dry analytical film chip has a difficulty in a photometry with a high accuracy. That is, the dry analytical film chip having a spreading layer composed of a porous material, such as fabric, nonwoven fabric and filter paper, hereinafter "fabric" is occasionally used as a representative of the above fibrous porous materials forms frays at edges of the spreading layer. Fiber dust generates from the frays, and adversely affects photometric results.

SUMMARY OF THE INVENTION

An object of the invention is to provide a dry analytical film chip capable of preventing the staining of an analyzer therefor at the side wall of the placing part of the incubator, the photometric portion, the discharging portion and the like caused by the effusion of liquid sample at edges of the dry analytical film chip.

Another object of the invention is to provide a dry analytical film chip capable of preventing the formation of frays (which are in a state of loosened and disordered but not cut into fine pieces yet) at edges of a spreading layer composed of fibrous porous material, such as fabric, nonwoven fabric of filter paper, and capable of further preventing the generation of fiber dust (which has been cut into fine pieces). (Hereinafter "frays" is occasionally called as the sum of fiber frays and fiber dust.)

The present invention provides a dry analytical film chip which has achieved the above object, comprising a support, at least one reagent layer, and a spreading layer laminated in this order, and comprising at least one of a means for preventing a liquid sample supplied onto and then spread into the spreading layer from reaching corner portions means for preventing from reaching corners, a means for preventing a liquid sample supplied onto and then spread into the spreading layer from reaching edges (means for preventing from reaching edges means for preventing from reaching edges), a means for preventing the formation of frays at edges of the spreading layer which is composed of a fibrous porous material (means for preventing the formation of frays), and a means for preventing a liquid sample supplied onto and then spread into the spreading layer from effusing out of edges (means for preventing from effusing out of edges), provided in the spreading layer.

1 Dry analytical film chip
2 Spreading layer
3 Nonporous portion made nonporous by fusion (means for preventing from reaching corners)
4 Nonporous portion made nonporous by fusion (means for preventing from reaching edges and/or means for preventing the formation of frays)
5 Nonporous portion made nonporous by fusion (means for preventing from reaching edges)
a Pressure zig—catching position
10 Dry analytical film chip
20 Dry analytical film chip storing portion
30 Dry analytical film chip conveying portion
40 Spotting portion
50 Incubator
51 Incubator body
52 Insertion hole
53 Placing part
54 Corner
55 Photometric window
56 Ring groove
57 Taper
58 Cover
59 Presser zig 60 Photometric portion 70 Discharging portion

DETAILED DESCRIPTION OF THE INVENTION

The spreading layer of the dry analytical film chip of the invention is provided with at least one of the means for preventing from reaching corners, the means for preventing from reaching edges, the means for preventing the formation of frays and the means for preventing from effusing out of edges. Two or more means of them may be provided.

The means for preventing from reaching corners is different from the means for preventing from reaching edges in their provided position, but their formation may be identical. The formation of the means for preventing from effusing out of edges may be identical with the means for preventing from reaching edges. The formation of the means for preventing the formation of frays may be identical with the means for preventing from reaching edges. The formation of the means for preventing from reaching edges, the means for preventing the formation of frays and the means for preventing from effusing out of edges may be identical. In the specification, edge includes corner.

In the invention, every means of the means for preventing from reaching corners, the means for preventing from reaching edges, the means for preventing the formation of frays and the means for preventing from effusing out of edges is composed by rendering corners, edges or their vicinity of the spreading layer composed of a porous material impermeable structure of liquid samples. Examples of the impermeable structure of liquid samples are formed by fusing the fiber or polymer constituting the matrix of the porous material and then cooling to solidify to render nonporous structure, or by clogging pores of the porous material with a hydrophobic or water-repellent or lipophilic material, such as hydrophobic ink, wax, curable polymer, curable paste or hot melt adhesive, or the like.

The means for preventing the formation of frays is to render a structure capable of preventing the formation of frays (which are loosened and disordered but not cut into fine pieces yet) and preventing the generation of fiber dust (which has been cut into fine pieces). An example of the structure capable of preventing the formation of frays and the generation of fiber dust is formed by heating to fuse the fiber of the fibrous porous material and then cooling to solidify. The fibrous porous material becomes substantially nonporous by fusing with heating followed by cooling to solidify, and accordingly, it also serves as the means for preventing from reaching corners and/or the means for preventing from reaching edges. The fibrous porous material, capable of preventing the formation of frays by heating to fuse fiber followed by cooling to solidify, includes fabrics (knitted fabrics, woven fabrics) of nylon, polyethylene terephthalate, mixed fabric of them and natural fiber such as cotton, and the like.

As the heating means for fusing the fiber or polymer constituting the matrix of the porous material, there are trowels with an electric heater, ultrasonic horn heads for ultrasonic welding, and heads for irradiating laser beams, every of which has a form to be fused. The thermal fusion by laser beam irradiation from a laser beam head can make the sectional area and the volume of the region, to which heat is added, small, and accordingly, the width of the region intercepting the permeation of a liquid sample formed by heating to fuse and then cooling to solidify can be made small compared with the fusion by the heating trowel or the ultrasonic horn head. Moreover, another advantage is that a spreading layer (in the embodiment of the dry analytical film chip comprising the spreading layer, a reagent layer and a support, all layers including the support) can be cut off simultaneously with the fusion of the fiber of the spreading layer by increasing the irradiation energy, and thereby, an independent cutting process can be omitted which is required in the fusion by the heating trowel or the ultrasonic horn head. That is, in the case of the heating by the heating trowel or ultrasonic heating, it is necessary to incorporate a cutting process for cutting by a cutting means, such as a cutter, the portion of a dry analytical film web of a laminate of a support, a reagent layer and a spreading layer, wherein the spreading layer is fused by the heating trowel or the ultrasonic horn head into a prescribed form. However, in the case of the laser beam irradiation, the spreading layer (in the embodiment of the dry analytical film chip comprising a spreading layer, a reagent layer and a support) can be cut off simultaneously with the fusion of the spreading layer into a prescribed form, by the irradiation of laser beam. In the dry analytical film chip, there is an embodiment of the spreading layer containing a reagent and of providing a reagent layer under the spreading layer, described later. In many cases, the reagent-containing spreading layer and the reagent layer contain enzyme weak which is on heat, and it was found that even heating to fuse the periphery of the spreading layer, the activity of the enzyme in the reagent-containing layer and the reagent layer does substantially not inactivated nor reduced. It was found that even heating to fuse the periphery of the spreading layer, the reagent components other than enzyme incorporated into the reagent-containing spreading layer or the reagent layer occasionally into other layer do not substantially degraded.

In the case of the thermal fusion by laser beam irradiation, the irradiation conditions of laser beam are set so as not to effuse liquid out of the edges of the porous spreading layer fused by heating followed by solidification. When not only the spreading layer is fused but also the support portion is fused to be cut off, the irradiation conditions are set so that the liquid effusion does not occur at edges of the porous spreading layer which have been fused and then solidified and so that the dry analytical film chip containing the support can be cut off simultaneously. As actual irradiation conditions, for example, in the case of carbon dioxide laser, are an output energy of about 10 W to about 25 W and a fusing speed of about 8 m/min to about 10 m/min for fusing to cut edges of a spreading layer, and an output energy of about 10 W to about 150 W and a fusing speed of about 1 m/min to about 20 m/min for fusing to cut not only the spreading layer but also the entire dry analytical film chip containing a support.

A means for clogging pores of the porous of the spreading layer composed of a porous material to render substantially nonporous is to clogg the pores with a hydrophobic (or water-repellent) or lipophilic material. As the material used for clogging, there are curable hydrophobic materials, waxes, curable polymers, curable pastes, hot melt adhesives, and the like, and examples are as follows:

Curable hydrophobic materials:
    Photo-setting or ultraviolet curing type adhesives, liquid photoresists Waxes:
    Solid waxes in plant origin (e.g. carnauba wax, cotton wax), solid waxes in animal origin (e.g. beeswax)

Curable polymers:
    Low melting or low softening point organic polymers (e.g. wax—formed polyethylene oxide, amorphous polyethylene)

Curable adhesives, curable pastes:
    Two-component epoxy resin adhesives
Hot—melt adhesives:
    Hot-melt adhesives having a low viscosity in a melted state (120 to 200° C.) and a high viscosity at ordinary temperature
Examples of Form:
    Sheet, string, thread
Hydrophobic materials:
    Inks for ball pen, inks for oily fast set writing utensil ("MAGIC INK", trade name, and homologs), inks for printing.
Water-repellent materials:
    Liquid or low melting point silicone polymers, liquid or low melting point fluorine-containing polymers The means for preventing from reaching corners is in a form wherein pores of the spreading layer at least at four corners (in the case that the form of the dry analytical film chip has no corner, such as circle or ellipsoid, the portions of the spreading layer caught by the presser zigs) and their vicinities are clogged (hereinafter, occasionally called "to clog pores"), or in a form wherein polymer constructing fibler or matrix of the porous material is rendered substantially nonporous by heating to fuse followed by cooling to solidify (hereinafter, occasionally called "to render nonporous by fusion"), so as to prevent a liquid sample from spreading to reach a position of the spreading layer caught by the presser zigs. An embodiment thereof is to clog pores or to render nonporous by fusion at portions including and being greater than the position caught by the top of each presser zig, and another embodiment is to clog pores or to render nonporous by fusion in line at portions on the side of center (inside) of the spreading layer from the position caught by the top of each presser zig.

The means for preventing from reaching edges and the means for preventing from effusing out of edges can be formed by to clog pores or to render nonporous by fusion in a form surrounding continuously the periphery of the prescribed spread form of which the center is the spotted portion of the spreading layer of the dry analytical film chip so as to prevent the effusion of a liquid sample spread to reach edges of the spreading layer out of the edges. When the means for preventing from edges is formed on the side of the center (inside) of the spreading layer from the positions caught by the presser zigs, the means also functions as the means for preventing from reaching corners. When the means for preventing from reaching edges or the means for preventing from effusing out of edges is formed on all edges of the spreading layer, in an embodiment having a fibrous spreading layer, since they also function as the means for preventing the formation of frays, they can prevent the formation of fiber frays and the generation of fiber dust at edge portions.

In every means of the means for preventing from reaching corners, the means for preventing from reaching edges, the means for preventing the formation of frays and the means for preventing from effusing out of edges, since the portions provided therewith can be held mechanically by forming them with a great area on the surface of the spreading layer, a conveying means of the dry analytical film chip other than suction pad can also been emplyed.

The dry analytical film chip of the invention is prepared by cutting a dry analytical film into a prescribed form. The fundamental structure of the dry analytical film chip is composed of a support, a reagent layer and a spreading layer laminated and integrated in this order.

To the underside of the support, a reinforcing sheet material or a thin plate material can be laminated for the purpose of strengthening the rigidity (nerve) of the support. All of the support, the reinforcing sheet material and the thin plate material function to keep the dry anlytical film chip flat. It is preferable that the support and the optional reinforcing sheet material and thin plate material are transparent. As the examples of the support, the reinforcing sheet material and the thin plate material, there are sheets of organic polymer, such as polyethylene terephthalate (PET), polystyrene or the like. In general, the reinforcing sheet material and the thin plate material are preferably made of an organic polymer having a great rigidity (nerve), and have a thickness similar to or thicker than the support. A suitable thickness of the support is about 100 $\mu$m to about 1,000 $\mu$m, preferably about 150 $\mu$m to about 300 $\mu$m. A suitable thickness of the reinforcing sheet material and the thin plate material is about 150 $\mu$m to about 1,000 $\mu$m, preferably about 180 $\mu$m to about 500 $\mu$m.

The form and size of the support and the optional reinforcing sheet material and thin plate material are not particularly limited within the range capable of keeping the flatness of the dry analytical film chip. Examples of the form are square, rectangle, circle and the like, and in general, the form is identical with the reagent layer described later. The size may be identical with, smaller than or greater than the reagent layer so far as keeping the flatness of the dry analytical film chip. When the support or the optional reinforcing sheet material or thin plate material has a form projected from the reagent layer, the projected portion can be nipped while conveying resulting in widening the range of selecting conveying means.

All of the support and the optional reinforcing sheet material and thin plate material are arranged, in general, so as to pass light. As the means for passing light, the support and the optional reinforcing sheet material or thin plate material theirselves are formed of a clear material capable of transmitting light, or are provided with a hole for passing light at the position where light passes upon photometry. As the material capable of transmitting light, there are various polymers excellent in transparency, such as polyethylene terephthalate (PET), polystyrene, acrylic polymers represented by polymethyl methacrylate, and the like. The hole for passing light can have any form capable of passing light upon photometry, and examples of form are circle, ellipsoid, square, rectangle or the like.

The reagent layer comprises at least one layer containing reagent components necessary for the coloring (dye-producing) or discoloring reaction for detecting an analyte (the object biochemical component to be determined) by subjecting to chemical reaction, biochemical reaction or immunological reaction directly or indirectly (through a prestage reaction), in a hydrophilic polymer binder, such as gelatin, polyacrylamide or polyvinyl alcohol. The reagent layer does not always require the reagent components, and is composed of a hydrophilic polymer binder alone such as in the dry analytical film for the determination of hemoglobin.

As the examples of the hydrophilic or weakly hydrophilic polymer binder having a film-forming ability, there are gelatin, gelatin derivatives, hydroxyalkyl cellulose, agarose, polyvinyl alcohol and the like. A known curing agent (crosslinking agent) may be blended with gelatin or gelatin derivatives.

The volume ratio of light-blocking particulates to hydrophilic polymer binder in the dry state is 10: about 2.5 to about 7.5, preferably about 3.0 to about 6.5. When the light-shielding particulates are titanium dioxide particulates, the ratio by weight of polymer binder is about 0.6 to about 1.8, preferably about 0.8 to 1.5 per 10 of titanium dioxide. The thickness of the light-blocking layer in the dry state is about 3 μm to about 30 μm, preferably about 5 μm to about 20 μm.

The spreading layer may be used by selecting from known fibrous porous materials and nonfibrous porous materials, Examples of the spreading layer are fibrous porous layers, such as woven fabric spreading layers disclosed in U.S. Pat. No. 4,292,272, U.S. Pat. No. 4,783,315, etc., such as, plain weaves including broad cloth and poplin, knitted fabric spreading layers disclosed in EP 0 162 302 A, etc., such as tricot, double tricot or milanese, and the spreading layers made of organic polymer fiber pulp-containing paper disclosed in Japanese Patent KOKAI No. 57-148250, nonfibrous isotropically porous spreading layers, such as, membrane filter (blushed polymer layer) disclosed in U.S. Pat. No. 3,992,158, continuous microspaces-containing porous layers where polymer particulates, glass particulates or diatomaceous earth are dispersed in a hydrophilic polymer binder, or continuous microspaces-containing porous layers where polymer particulates are joined so as to contact with each other at a point by using a polymer adhesive which dose not swell in water (three-dimensional lattice structure layer), the spreading layers excellent in blood cell-separating ability composed of plural porous layers (e.g. a combination of two layers of a woven fabric or knitted fabric and a membrane filter, a combination of three layeres of a woven fabric or knitted fabric) of which each interface is joined to laminate by disposing an adhesive in fine discontinuous dots or strips (half-tone dots in printing field) disclosed in U.S. Pat. No. 5,019,347, EP 0 226 465 A, etc.

In the specification, the dry analitical film chip includes test elements in filter paper type and single layer or multilayer test elements modified thereof laminated to the aforementioned support by a suitable known adhesive.

The form of the dry analytical film chip is, in general, square, rectangle, circle, ellipsoid or the like, having a side of about 10 to 20 mm in the case of square and rectangle, a diameter (both of the major axis and the minor axis) of about 10 to 20 mm in the case of circle and ellipsoid, and the thickness is about 350 μm to 1.5 mm. In view of analytical operation and manufacture, square and rectangle near square are preferred.

As the biological components analyzable by the dry analytical film chip of the invention, there are blood sugar (glucose), cholesterol, urea nitrogen (BUN), creatinine, bilirubin, hemoglobin, glutamic-oxaloacetic transaminase (GOT), glutamic-pyruvic transaminase (GPT), amylase, c-reactive protein (CRP), and the like.

In the first aspect of the dry analytical film chip of the invention, the means for preventing from reaching corners is provided in the spreading layer, and prevents staining of the presser zigs by adhering a liquid sample to the top of the presser zigs by preventing the liquid sample from reaching corners of the spreading layer caught by the presser zigs of an incubator from the spotting portion located at almost the center of the dry analytical film chip.

In the second aspect of the dry analytical film chip of the invention, the means for preventing from reaching edges is provided in the spreading layer, and prevents the effusion of a liquid sample out of edges of the spreading layer, prevents staining of the incubator, the photometric portion, the discharging portion or the like of an analyzer by adhering the liquid sample, and prevents staining of another dry analytical film chip which has been spotted with a liquid sample but not measured photometrically yet, by preventing the liquid sample from reaching edges from the spotting portion located at almost the center of the dry analytical film chip.

In the third aspect of the dry analytical film chip of the invention, the means for preventing the formation of frays is provided in the spreading layer which is composed of a fibrous material, such as fabric, nonwoven fabric or filter paper, and prevents the formation of frays and the generation of fiber dust at the edges of the spreading layer, and as a result, adverse affects on photometric results are eliminated.

In the fourth aspect of the dry analytical film chip of the invention, the means for preventing from effusing out of edges (doubled as the means for preventing from reaching corners) is provided in the spreading layer, and prevents the effusion of a liquid sample out of edges of the spreading layer, prevents staining of the incubator, the photometric portion, the discharging portion or the like of an analyzer by adhering the liquid sample, prevents staining of another dry analytical film chip which has been spotted with a liquid sample but not measured photometrically yet by adhering the previous liquid sample, by preventing the liquid sample from reaching edges (including corners) from the spotting portion located almost the center of the dry analytical film chip, and prevents staining of the presser zigs by adhering the liquid sample to the top of the presser zigs by preventing the liquid sample from reaching corners caught by the presser zigs of the incubator from the spotting portion located almost the center of the dry analytical film chip.

Furthermore, in every one of the above first, second, third and fourth aspect of the dry analytical film chip of the invention, it is prevented to stain dry analytical film chips loaded later into the placing part of the incubator of an analyzer by the liquid sample already adhered to the pacing part or the presser zigs. Since a liquid sample does not effuse out of edges of the spreading layer, the spotting amount of a liquid sample can be increased to improve measuring accuracy. Since it is not necessary to be so accurate positioning of spotting a liquid sample onto the center of the dry analytical film chip, a spotting apparatus therefor can be made inexpensive because of not so severe requirement for the accuracy of pepette tips for spotting a liquid sample and the like.

EXAMPLES

Figure 1:
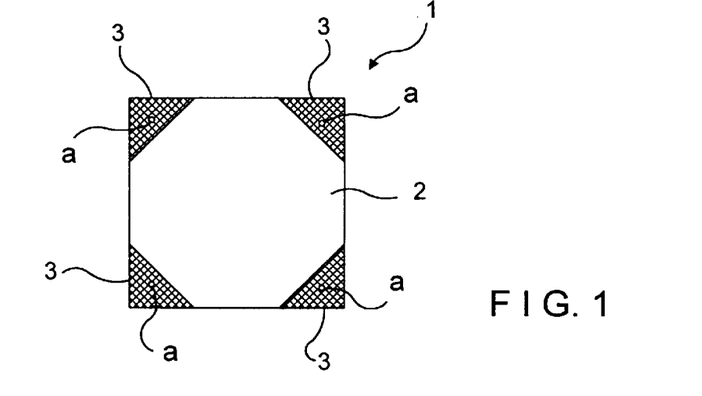
FIGS. 1, 2, 3 and 4 are plan views of dry analytical film chips of the invention provided with the means for preventing from reaching corners in the spreading layer.

Some examples of the dry analytical film chip of the invention are illustrated in FIGS. 1 though 12.

In the examples, each fibrous spreading layer was subjected to the heating to fuse treatment under the following conditions:

The knitted fabric formed of 100% polyester (polyethylene terephthalate) about 150 μm to about 300 μm in thickness and the plain weave fabric formed of 100% polyester about 150 μm to about 200 μm in thickness were treated at 350° C. to 450° C. for 0.1 to 0.5 second.

The knitted fabric of formed of mixed fiber of 65% polyester and 35% cotton about 150 μm to about 300 μm in thickness and the plain weave fabric formed of mixed fiber of 65% polyester and 35% cotton about 150 μm to about 200 μm in thickness were treated at 500° C. for 0.2 to 0.5 second.

The dry analytical film chips illustrated in FIGS. 1 through 4 are examples of the first aspect of the invention provided with the means for preventing from reaching corners in the spreading layer.

In the dry analytical film chip 1 shown in FIG. 1, four fused portions 3 were formed as the means for preventing from reaching corners into triangle at all corner portions of the spreading layer containing the position "a" caught by the presser zig for the spreading layer by heating to fuse the corner portions of the spreading layer and then cooling the solidify by allowing to stand at room temperature or blowing cooling air to render sabstantially nonporous. A reagent layer and a support (both are not illustrated) are provided under the spreading layer 2.

Figure 2:
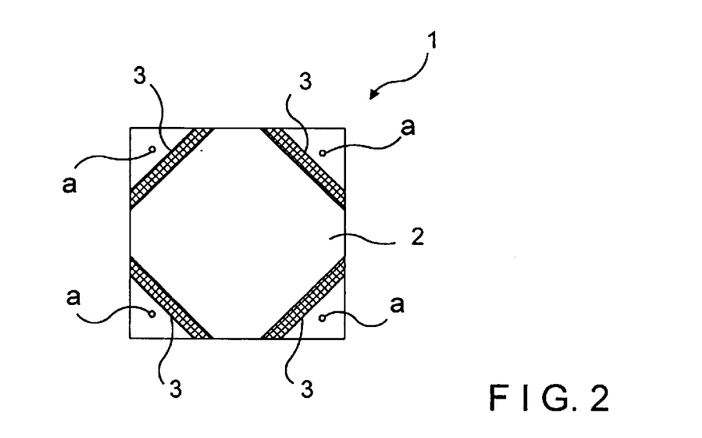

In the dry analytical film chip 1 shown in FIG. 2, four fused portions 3 were formed as the means for preventing from reaching corners into band at the four corner portions on the inside than the position "a" caught by the presser zig for the spreading layer bridging two adjacent edges by heating to fuse the band portions of the spreading layer and then cooling to solidify by allowing to stand at room temperature or blowing cooling air to render substantically nonporous.

Figure 3:
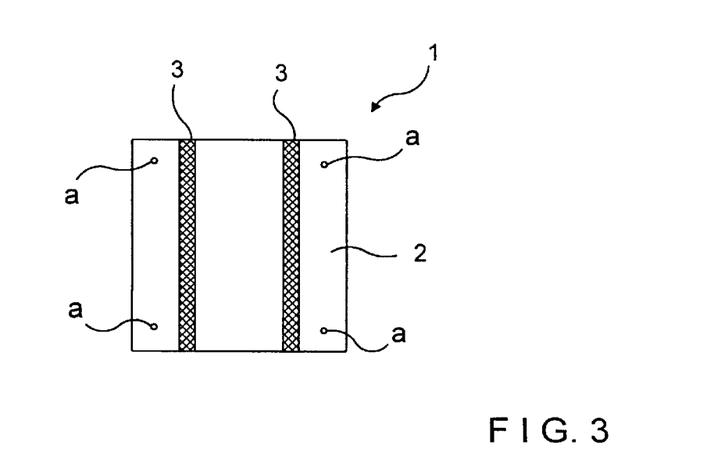

In the dry analytical film chip 1 shown in FIG. 3, two fused portions 3 were formed as the means for preventing from reaching corners into band on the inside than the position "a" caught by the presser zig for the spreading layer bridging two edges opposite to each other in parallel by heating to fuse the band portions of the spreading layer and then cooling to solidify by allowing to stand at room temperature or blowing cooling air to render substantically nonporous.

Figure 4:
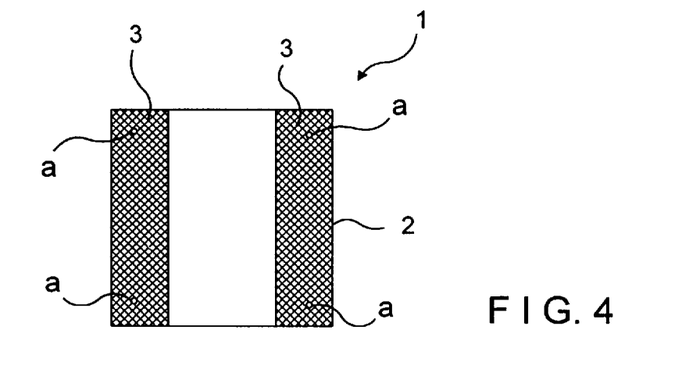

In the dry analytical film chip 1 shown in FIG. 4, two fused portions 3 were formed as the means for preventing from reaching corners into wide band at two opposite edges containing the position "a" caught by the presser zig for the spreading layer by heating to fuse the band portions of the spreading layer and then cooling to solidify by allowing to stand at room temperature or blowing cooling air to render substantically nonporous.

The dry analytical film chips illustrated in FIGS. 5 through 12 are examples of the second aspect of the invention provided with the means for preventing from reaching edges in the spreading layer. Some examples double as an example of the first aspect of the invention provided with the means for preventing from reaching corners or an example of the third aspect of the invention provided with the means for preventing the formation of frays in the spreading layer.

Figure 5:
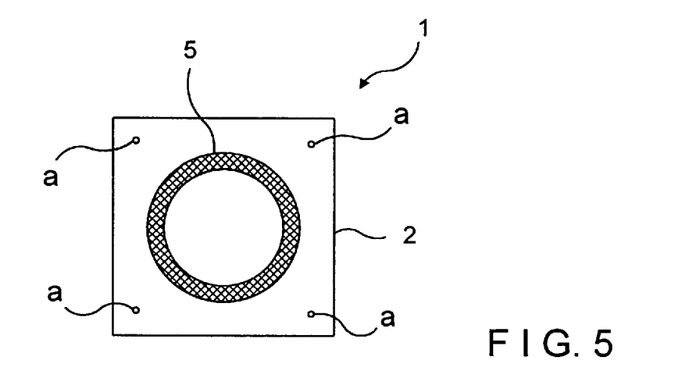
FIGS. 5, 6, 7, 8, 9, 10, 11 and 12 are plan views of dry analytical film chips of the invention provided with the means for preventing from reaching edges in the spreading layer. The means shown in FIG. 5 doubles as the means for preventing from reaching corners. The means shown in FIG. 6 doubles as the means for preventing the formation of frays. The means shown in FIGS. 7 through 12 triples as the means for preventing from reaching corners and the means for preventing the formation of frays.

In the dry analytical film chip shown in FIG. 5, a fused portion 5 was formed as the means for preventing from reaching edges into band to form an open circle on the inside than the position "a" caught by the presser zig for the spreading layer by heating to fuse the band portions of the spreading layer and then cooling to solidify by allowing to stand at room temperature or blowing cooling air to render substantially nonporous. The fuse portion 5 in this example also functions as the means for preventing from reaching corners.

Figure 6:
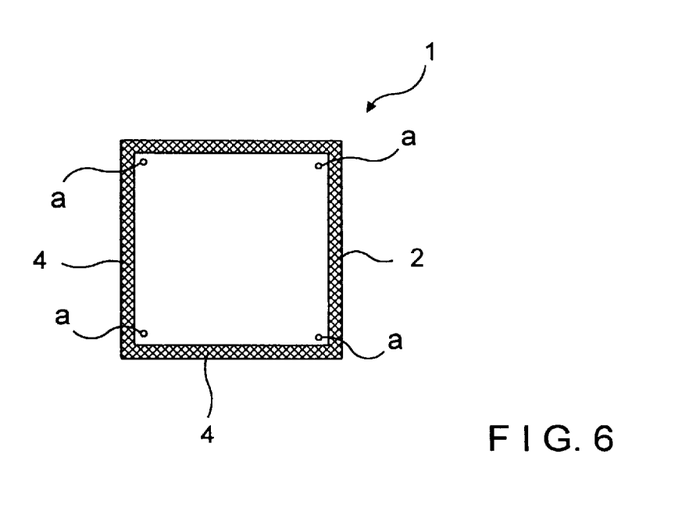

In the dry analytical film chip shown in FIG. 6, a fused portion was formed as the means for preventing from reaching edges into band at all edges to form an open square on the outside than the position "a" caught by the presser zig for the spreading layer by heating to fuse the band portions of the spreading layer and then cooling to solidify by allowing to stand at room temperature or blowing cooling air to render substantially nonporous. The fused portion 4 can prevent the formation of fiber frays at edges of the spreading layer 2, when it comprises a fibrous spreading layer.

Figure 7:
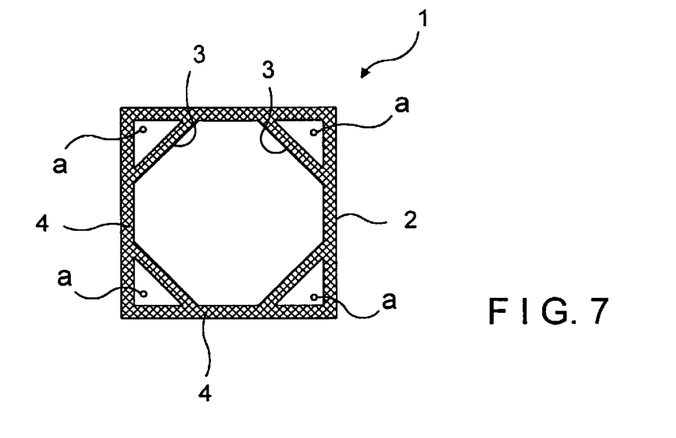

In the dry analytical film chip shown in FIG. 7, a fused portion 4 was formed as the means for preventing from reaching edges into band at all edges to form an open suqare on the outside than the position "a" caught by the presser zig for the spreading layer and, four fused portions 3 were formed as the means for preventing from reaching corners into band bridging all of adjacent edges on the inside than the position "a" caught by the presser zig for the spreading layer, by heating to fuse the band portions of the spreading layer and then cooling to solidify by allowing to stand at room temperature or blowing cooling air to render substantially nonporous. This example also exercises the function of the means for preventing from reaching corners, and in the embodiment comprising a fibrous spreading layer, it can prevent the formation of fiber frays at edges of the spreading layer 2.

Figure 8:
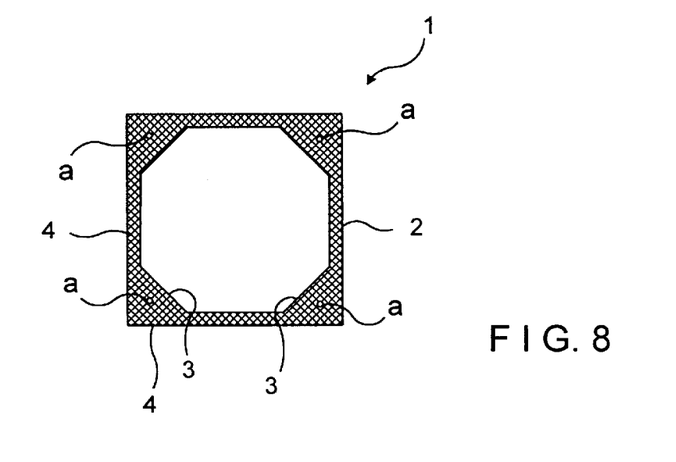

In the dry analytical film chip shown in FIG. 8, a fused portion 4 was formed as the means for preventing from reaching edges into band at all edges to form an open square and, four fused portions 3 were formed as the means for preventing from reaching corners into triangle at all corner portions of the spreading layer containing the position "a" caught by the presser zig for the spreading layer, by heating to fuse the portions of the spreading layer and then cooling to solidify by allowing to stand at room temperature ar blowing cooling air to render substantially nonporous. This example also exercises the function of the means for preventing from reaching corners, and in the embodiment comprising a fibrous spreading layer, it can prevent the formation of fiber frays at edges of the spreading layer 2.

Figure 9:
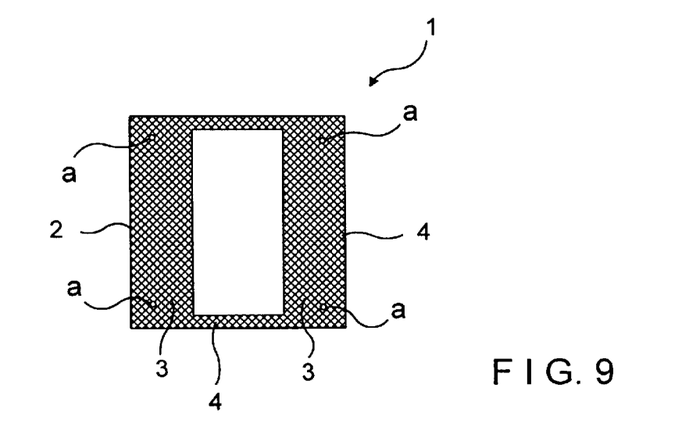

In the dry analytical film chip shown in FIG. 9, a fused portion 4 was formed as the means for preventing from reaching edges into band at all edges to form an open square by heating to fuse the portions of the spreading layer and then cooling to solidify by allowing to stand at room temperatuer or blowing cooling air to render substantially nonporous. The fused portion 3 was widened as the means for preventing from reaching corners at two opposite edges so as to contain the positions "a" caught by the presser zigs for the spreading layer. This example also exercises the function of the means for preventing from reaching corners, and in the embodiment comprising a fibrous spreading layer, it can prevent the formation of fiber frays at edges of the spreading layer 2.

Figure 10:
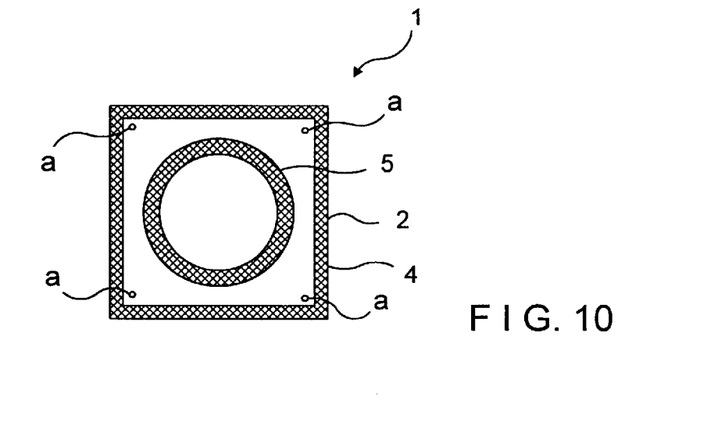

The dry analytical film chip shown in FIG. 10 is a combination of the dry analytical film chips of FIGS. 5 and 6, and functions as the means for preventing from reaching corners, and in the embodiment comprising a fibrous spreading layer, it can prevent the formation of fiber frays at edges of the spreading layer 2, as well as the means for preventing from reaching edges.

Figure 11:
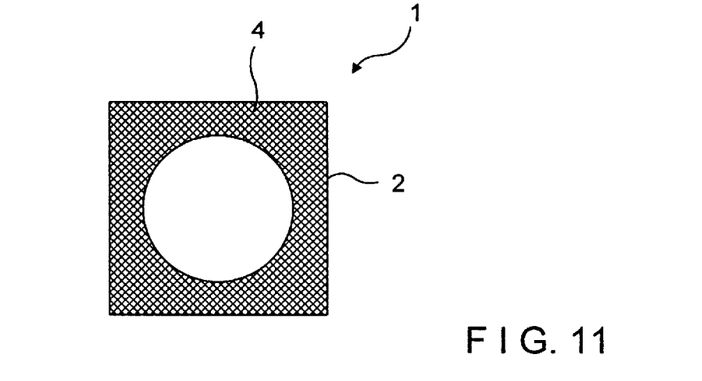

In the dry analytical film chip shown in FIG. 11, a fused portion 4 was formed as the means for preventing from reaching edges entirely except leaving the center into circle greatly, by heating to fuse the band portions of the spreading layer and then cooling to solidify by allowing to stand at room temperature or blowing cooling air to render substantially nonporous. This example also exercises the function of the means for preventing from reaching corners, and in the embodiment comprising a fibrous spreading layer, it can prevent the formation of fiber frays at edges of the spreading layer 2.

Figure 12:
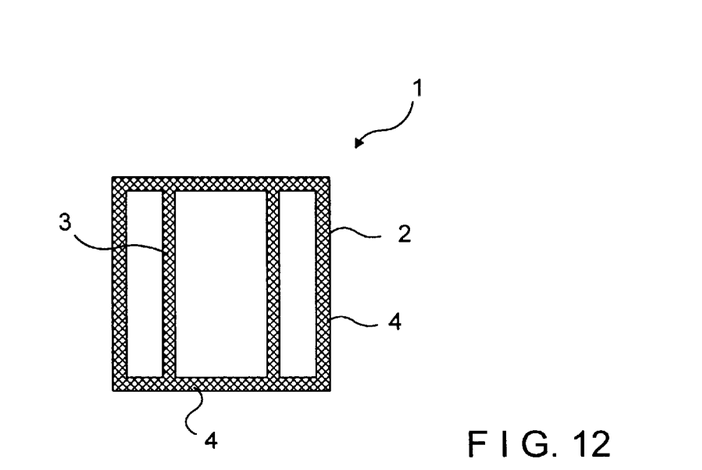

The dry analytical film chip shown in FIG. 12 is a combination of the dry analytical film chip of FIGS. 3 and 6, and functions as the means for preventing from reaching corners, and in the embodiment comprising a fibrous spreading layer, it can prevent the formation of fiber frays at edges of the spreading layer 2, as well as the means for preventing from reaching edges.

In the above examples shown in FIGS. 1 through 12, although all of the means for preventing from reaching corners, the means for preventing from reaching edges and the means for preventing the formation of frays were formed by heating to fuse the band portions of the spreading layer and then cooling to solidify by allowing to stand at room temperature or blowing cooling air to render substantially nonporous, the means for preventing from reaching corners, the means for preventing from reaching edges and the means for preventing the formation of frays in a form shown in FIGS. 1 through 12 can be formed by clogging the pores of the spreading layer with a hydrophobic (or water-repellent) or lipophilic material. Preferable materials for clogging the pores are waxes in solid at ordinary temperature, polyethylene oxide wax, amorphous polyethlene, hot melt adhesive, liquid photoresists, and the like.

We claim:

1. A dry analytical substantially flat film chip for use as an analytical element for liquid samples comprising a support, at least one reagent layer, and a porous thermoplastic spreading layer laminated over the whole area of each layer in this order and suitable, as is, for use as an analytical element, and having means for restraining a liquid sample applied to the surface of the spreading layer to a predetermined area of the surface, said reagent layer comprising a hydrophilic polymer binder and reagent components necessary for a coloring or discoloring reaction for detecting an analyte, and said restraining means comprising a fused nonporous area positioned so as to prevent liquid sample applied to the spreading area from spreading beyond the predetermined area.

2. The film chip of claim 1 wherein the means for restraining a liquid sample applied to the surface is formed by heating the chip to fuse the spreading layer and then allowing the chip to cool to solidify the fused layer, said heating being carried out by use of a laser beam head at an output energy of 10 to 150 W.

3. The film chip of claim 1 wherein the spreading layer is formed from a member selected from the group consisting of woven fabric, knitted fabric, and nonwoven fabric.

4. The film chip of claim 1 wherein the means for restraining a liquid sample also functions as a means for preventing the formation of fiber frays at and edge of the spreading layer.

5. The film chip of claim 1 wherein said predetermined area excludes corner portions so as to prevent liquid sample applied to the spreading area from spreading to corner portions.

6. The film chip of claim 1 wherein said reagent components include an enzyme.

7. The film chip of claim 1 wherein said hydrophilic polymer binder is selected from the group consisting of gelatin, gelatin derivatives, polyacrylamide, hydroxy alkyl cellulose, agarose and polyvinyl alcohol.

8. The film chip of claim 1 wherein said hydrophilic polymer binder is selected from the group consisting of gelatin, polyacrylamide and polyvinyl alcohol.

9. The film chip of claim 1 wherein the fused nonporous area extends inside the edges of the film chip.

10. The film chip of claim 1 wherein the fused nonporous area is spaced from the edges of the film chip.

11. A dry analytical substantially flat film chip for use as an analytical element for liquid samples comprising a support, at least one reagent layer, and a porous thermoplastic spreading layer laminated over the whole area of each layer in this order and suitable, as is, for use as an analytical element, and having means for restraining a liquid sample applied to the surface of the spreading layer to a predetermined area of the surface, said reagent layer comprising a hydrophilic polymer binder and reagent components necessary for a coloring or discoloring reaction for detecting an analyte, and said restraining means comprising an area of the spreading layer clogged with a hydrophobic or lipophilic material to render it nonporous and positioned so as to prevent liquid sample applied to the spreading area from spreading beyond the predetermined area.

12. The chip of claim 11 wherein the area of the spreading layer is clogged by immersion of the spreading layer in a hydrophobic or lipophilic material.

13. The chip of claim 11 wherein the spreading layer is formed from a member selected from the group consisting of woven fabric, knitted fabric, and nonwoven fabric.

14. The chip of claim 11 wherein the means for restraining a liquid sample also functions as a means for preventing the formation of fiber frays at an edge of the spreading layer.

15. The film chip of claim 11 wherein said predetermined area excludes corner portions so as to prevent liquid sample applied to the spreading area from spreading to corner portions.

16. The film chip of claim 11 wherein said reagent components include an enzyme.

17. The film chip of claim 11 wherein said hydrophilic polymer binder is selected from the group consisting of gelatin, gelatin derivatives, polyacrylamide, hydroxy alkyl cellulose, agarose and polyvinyl alcohol.

18. The film chip of claim 11 wherein said hydrophilic polymer binder is selected from the group consisting of gelatin, polyacrylamide and polyvinyl alcohol.

* * * * *